(12) United States Patent
Samson

(10) Patent No.: US 6,762,875 B2
(45) Date of Patent: Jul. 13, 2004

(54) CREATING REFRACTIVE INDEX CHANGES IN GLASS BY UP-CONVERSION OF RARE EARTH IONS

(75) Inventor: Bryce N. Samson, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 287 days.

(21) Appl. No.: 10/071,309

(22) Filed: Feb. 7, 2002

(65) Prior Publication Data

US 2003/0147119 A1 Aug. 7, 2003

(51) Int. Cl.[7] .............................. G02F 2/02; C03C 4/08; C03C 4/10; C03C 4/12
(52) U.S. Cl. .................... 359/326; 501/13; 501/126; 501/904; 501/905
(58) Field of Search ................... 359/326–332; 501/13, 126, 904, 905

(56) References Cited

U.S. PATENT DOCUMENTS

| | | | | |
|---|---|---|---|---|
| 5,436,919 A | * | 7/1995 | Chwalek et al. | 372/7 |
| 5,786,102 A | * | 7/1998 | Paz-Pujalt et al. | 428/689 |
| 2003/0011751 A1 | * | 1/2003 | Sakata et al. | 353/30 |
| 2003/0118841 A1 | * | 6/2003 | Horne et al. | 428/425.9 |
| 2004/0037538 A1 | * | 2/2004 | Schardt et al. | 385/142 |

OTHER PUBLICATIONS

"A Photopolymerizable Glass with Diffraction Efficiency Near 100% for Holographic Storage", Applied Physics Letters, vol. 78, No. 11, Mar. 12, 2001, Cheben et al, pp. 1490–1492.

* cited by examiner

Primary Examiner—John D. Lee
(74) Attorney, Agent, or Firm—Siwen Chen; Mary Y. Redman

(57) ABSTRACT

A method for creating refractive index changes in a substrate is provided by irradiating the substrate with infrared (IR) or visible light radiation. Ultra-violet (UV) radiation is generated in the substrate responsive to the IR or visible light radiation such that the change in the refractive index of the substrate is generated responsive to the UV radiation. Preferably, the substrate comprises a glass doped with rare earth ions.

34 Claims, 9 Drawing Sheets

CREATING REFRACTIVE INDEX CHANGES IN GLASS BY UP-CONVERSION OF RARE EARTH IONS

BACKGROUND OF THE INVENTION

1. Field of the Invention

The invention relates generally to methods for creating refractive index changes in substrates and waveguides, and more particularly, to methods for creating refractive index changes by up-conversion of rare earth ions.

2. Technical Background

Creating refractive index changes in substrate materials, such as glass, is a very useful process that may be used to create waveguide structures. In addition to creating the waveguide, it is also useful to modify the refractive index profile of an existing waveguide (e.g. optical fiber) to make grating structures. Alternatively, modifying the refractive index profile may be used as an optical storage medium, as used in producing *holographic* images for example.

Presently, refractive index changes in optical fiber are created by a number of conventional processes. One such technique utilizes two photon absorption of blue (e.g. 488 nm) light from an Argon ion laser. The blue photons are absorbed by the glass. The absorption of the photons by the glass generates refractive index changes in the glass. The manufacture of very long gratings (e.g. meters in length) may be well suited by this technique since the exposure occurs simultaneously along the whole fiber length.

This technique, however, is relatively expensive. High power blue lasers are required to cause a sufficient amount of photon absorption to obtain the desired change in the refractive index to occur. Such lasers are generally very expensive.

Even when these expensive blue lasers are used, they are best suited to only certain types of optical fiber. Although silica fiber is transparent to blue light, standard fiber is highly multi-moded at blue photon wavelengths having a cutoff wavelength in the IR. However, most practical applications would require the fiber to be single moded at the writing wavelength, hence requiring special fiber for this application.

Another technique utilizes ultra violet (UV) light that is absorbed by the glass creating defects in the glass, which generates the desired refractive index changes. The UV light is commonly in the range of about 248 nm to about 193 nm. A dopant is often incorporated into a portion of the glass material (typically core material) to strongly increase the UV absorption to create refractive index changes. Common silica glass dopants include germanium, boron, tin, and cerium. For these dopants, absorption will generally be very strong, for example in the range of 0.1 dB to about 100 dB per micron.

The strong absorption results in limited penetration depth of the UV light. Consequently, conventional UV manufacturing techniques cannot propagate UV light along the optical fiber, as the penetration depth is not deep enough to propagate along the whole length of the optical fiber. Instead, conventional UV manufacturing techniques expose the side of the optical fiber, one section at a time. Side exposure is limited by the phase mask size which is usually less than 10 cm at best, and the UV beam diameter which determines penetration depth of the UV light. Thus conventional UV manufacturing techniques are only capable of creating refractive index changes in sections of less than 10 cm in length. To create a refractive index change in substrates longer than 10 cm, the entire setup must be moved to the corresponding next 10 cm section, realigned, and run again. As exposure to the UV light may take several hours to create the refractive index changes, long lengths of substrate cannot be manufactured quickly using a conventional UV light process. Further, moving the entire setup requires extremely careful setup to align the refractive index changes of the corresponding sections, or else the refractive index change will not be uniform throughout the optical fiber, and will not have the tolerances required for optical signal transmission.

Creating waveguide structures in bulk substrate materials can be achieved by a number of different mechanisms. Using light to directly create the refractive index change is either done by direct absorption of UV light into the bandgap of the material, which again suffers from strong absorption and hence limited penetration depth, or very high order multiphoton absorption typically using high intensity short pulse (100 fsec) lasers. Very high order multiphoton absorption suffers from the expense and complication of the required laser sources, as well as the difficult control over the non-linear propagation of ultra short pulses through the substrate material, often resulting in non-optimized waveguides.

SUMMARY OF THE INVENTION

One aspect of the present invention includes providing a method for creating refractive index changes in a substrate by irradiating the substrate with infrared (IR) radiation or visible light. Ultra-violet (UV) radiation is generated in the substrate responsive to the IR radiation such that the change in the refractive index of the substrate is generated responsive to the UV radiation. Preferably, the substrate includes a glass doped with rare earth ions. The rare earth ions may include at least $Tm^{3+}$ ions.

Another aspect of the present invention is directed to a substrate including a substrate matrix material, at least one type of rare earth ion dopant in the matrix material, and at least one defect in the matrix material which affects a refractive index of the substrate, and which was created by ultra-violet (UV) radiation emission from the rare earth ion dopants responsive to infrared (IR) radiation. Preferably, the UV radiation is created by an up-conversion process that converts IR radiation or visible radiation to UV radiation. The substrate may include an optical fiber, whose core is doped with $Tm^{3+}$ ions.

Another aspect of the present invention includes a method of making a glass substrate including the steps of doping the glass substrate with fluorescent ions, and pumping infrared (IR) radiation or visible light radiation into the glass substrate. Ultra-violet (UV) radiation is generated in the substrate by the fluorescent ions responsive to the IR or visible radiation to create defects in the substrate such that a change in a refractive index is generated. Preferably, the step of pumping IR or visible radiation is performed by a semiconductor pump laser.

BRIEF DESCRIPTION OF THE DRAWINGS

The foregoing advantages and features of the invention will become apparent upon reference to the following detailed description and the accompanying drawings, of which.

DETAILED DESCRIPTION OF SPECIFIC EMBODIMENTS

Reference will now be made in detail to present embodiments of the invention. Wherever possible, the same reference numbers will be used throughout the drawings to refer to the same or like parts.

The present invention relates generally to creating refractive index changes in substrates. More specifically, the present invention provides a process for creating refractive index changes utilizing UV light by up-conversion of rare earth ions.

Figure 1:
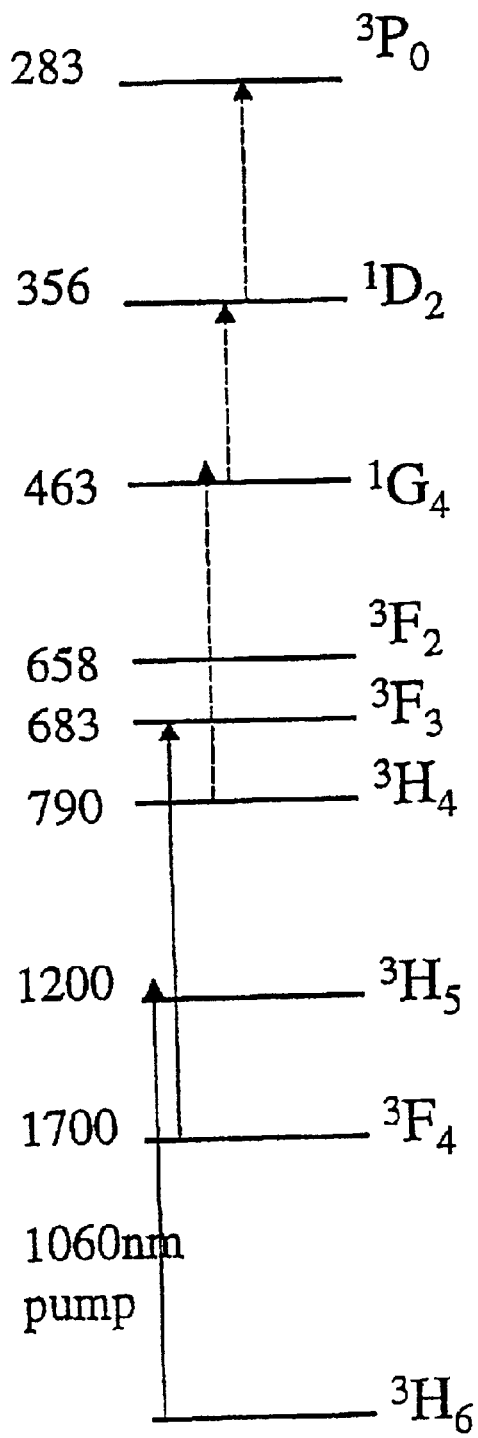
FIG. 1 is an energy level diagram of a $Tm^{3+}$ ion.

It has been determined that refractive-index changes can be created by propagating infrared radiation (IR) or visible light along the length of the substrate (e.g. optical fiber), which is converted to UV light by a dopant in the glass material. As is well known in the art, ions comprise multiple energy levels that may absorb and/or emit photons of light. Energy levels for Thulium$^{3+}$ ($Tm^{3+}$), one such ion, are shown in the energy diagram of FIG. 1. As the inventor has discovered, $Tm^{3+}$ absorbs wavelengths in the range of about 1000 nm to about 1250 nm, preferably 1060 nm, thereby promoting the ion from the 3H6 energy level to the 3H5 energy level. Further, promotion up to the 3P0, 1D2, and 1G4 energy levels by up-conversion via further photon absorption (e.g., excited state absorption) is a phenomenon well known in the art with respect to various ions at specific wavelengths. The inventor has discovered that as an excited $Tm^{3+}$ ion tries to return from the excited states to the "normal" 3H6 energy level, it emits UV photons at about 290 nm for 3P0, about 350 nm for 1D2, and about 470 nm for 1G4. Thus UV light at about 290 nm, about 350 nm, and about 470 nm is generated by the excited $Tm^{3+}$ ion responsive to infrared (IR) radiation at about 1060 nm.

Figure 9:
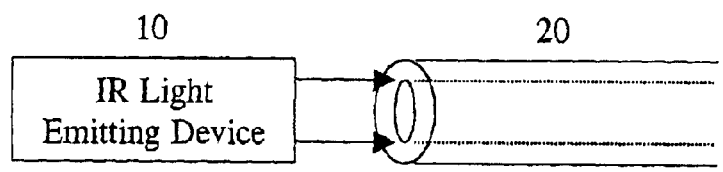
FIG. 9 is a block diagram of a first embodiment according to the present invention.

A first embodiment of a method for creating refractive index changes in a substrate is shown by the block diagram of FIG. 9. This first embodiment includes irradiating the substrate 20 with IR radiation. While an embodiment that uses IR radiation is described for illustrative purposes, it will be understood that other wavelength bands such as visible light can be used. In the illustrated embodiment, preferably the IR radiation propagates along the length of the substrate 20. The dopants absorb the IR radiation and, as they try to return to a normal state, emit UV radiation. A local change in the refractive index of the substrate is caused by the UV radiation.

The substrate 20 is irradiated by at least one IR light emitting device 10. The device 10 generates IR radiation with at least one pre-selected wavelength that generates a population up-conversion in the substrate 20. Preferably, the IR radiation contains at least one wavelength in the range of about 600 nm to about 1500 nm, more preferably at least one wavelength in the range of about 1000 nm to about 1250 nm, and most preferably at least a wavelength of about 1060 nm. The inventor has discovered that a low power cw IR source of about 300 mW at about 1060 nm generates sufficient IR radiation for creating a refractive index change in a 4 μm diameter optical fiber 1 meter in length. Further, more than one IR wavelength may be used to promote up-conversion to specific energy levels depending on the desired parameters in the optical fiber, and improve the speed of creating the refractive index changes. Low power cw IR sources are substantially less expensive than blue power lasers and short pulse (100 fsec) high energy lasers, thereby reducing the manufacturing cost of optical fibers formed according to the present invention. Further, due the low operating power of low power cw IR sources, the present invention does not suffer from non-linear interaction with the host materials as occurs in short pulse (100 fsec) high energy laser schemes.

A typical substrate 20 comprises a glass doped with rare earth ions to facilitate up-conversion emission of UV light responsive to IR radiation or visible light. Typical rare earth ion dopants include one or more of $Pr^{3+}$, $Er^{3+}$, $Eu^{3+}$, $Nd^{3+}$, $Ho^{3+}$, $Sm^{3+}$, $Tb^{3+}$, and $Dy^{3+}$ ions. Preferably, the rare earth ion dopant comprises $Tm^{3+}$ ions. Other fluorescent ions (not just rare earth ions) may also be used, where the fluorescent ions emit electromagnetic radiation, especially of UV light, stimulated by the absorption of IR or visible radiation and persisting as long as the radiation is continued. The choice of ions used may be chosen so that up-conversion is characterized by an emitted radiation of a wavelength shorter than the pump wavelength. Where an index of refraction change is desired to be generated by propagation of emitted UV radiation, the pump wavelength can be chosen to be longer than UV radiation. Typical glass compositions include Sb-silicate glass, germanate glass, and tellurite glass. The inventor has also found that this process can be used to create waveguides in other substrate 20 materials, such as polymers.

By way of example, in a case where a $Tm^{3+}$ dopant is used, the IR radiation increases the 3F4 level population of the $Tm^{3+}$ ions. At least one of the 1D2 level population and the 3P0 level population of the ions is increased by up-conversion of the 3F4 level population, resulting in the ion emitting UV radiation. The UV radiation creates defects in the substrate which cause a change in the refractive index of the substrate.

Figure 2:
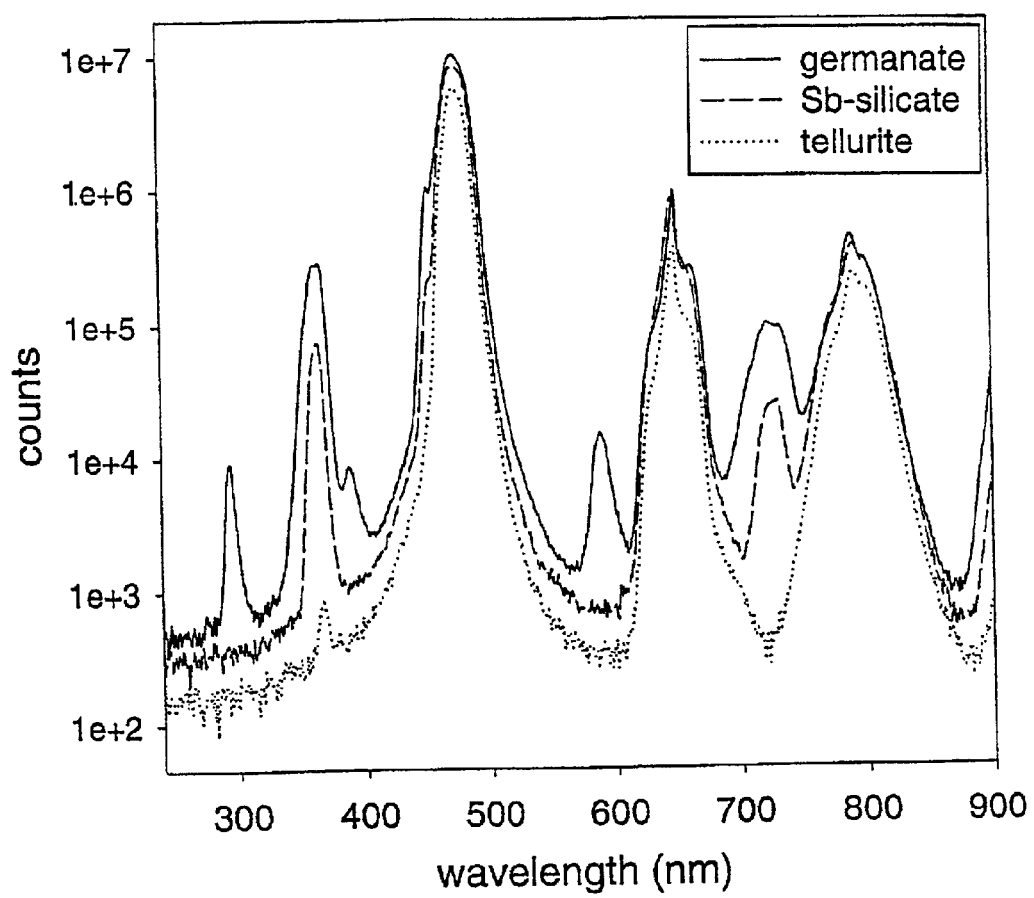
FIG. 2 is a graph showing up-conversion fluorescence for various $Tm^{3+}$ doped glasses.

Examples of fluorescence at UV wavelengths of $Tm^{3+}$ in various glass materials are shown in FIG. 2. Germanate glass, Sb-silicate glass, and tellurite glass were doped with $Tm^{3+}$ ions. The $Tm^{3+}$ ions were excited by a low power 1120 nm IR light emitting device. This device was used because the strongest absorption for $Tm^{3+}$ ions occurs at 1120 nm. FIG. 2 shows the highest order up-conversion fluorescence at 290 nm for germanate, 360 nm for Sb-silicate and 480 nm for tellurite glasses respectively. Thus, FIG. 2 clearly demonstrates generation of UV light from the $Tm^{3+}$ ions by up-conversion of absorbed IR radiation.

Figure 3:
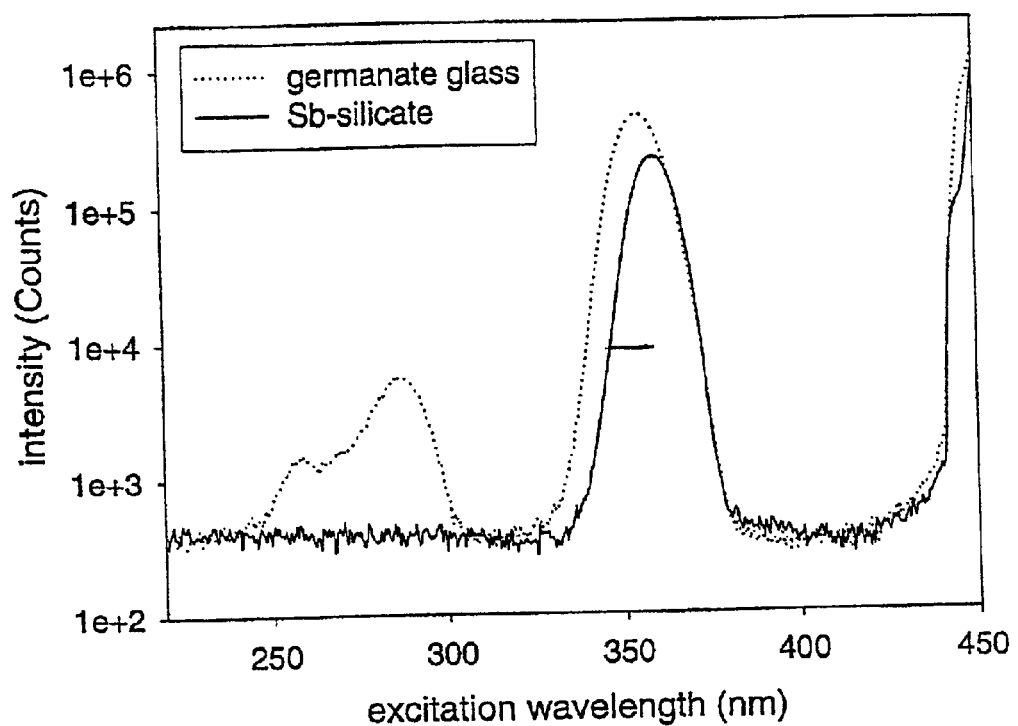
FIG. 3 is a graph showing the excitation spectra for two $Tm^{3+}$ doped glasses.
Figure 4:
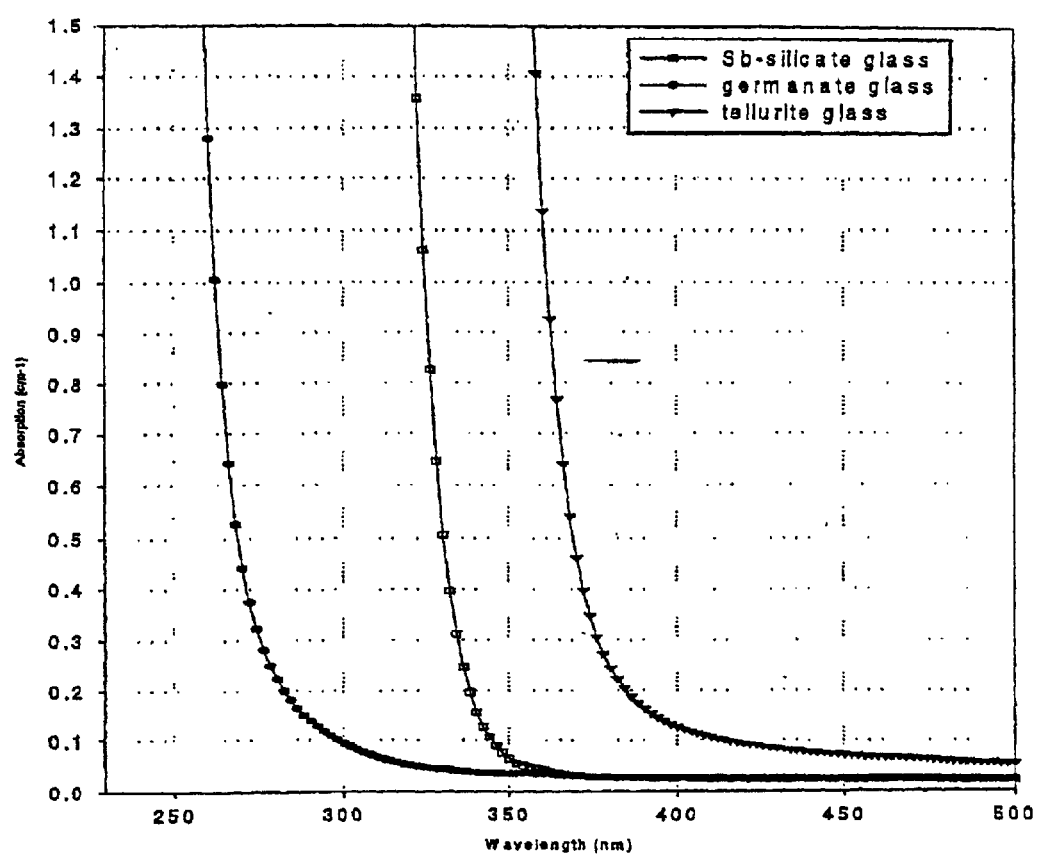
FIG. 4 is a graph showing the wavelength absorption edge for three $Tm^{3+}$ doped glasses.

The glass materials absorb the wavelengths of UV light generated by the $Tm^{3+}$ ions. The graph of FIG. 4 shows the glass absorption edges occur at about 280 nm for germanate, about 340 nm for Sb-silicate and about 380 nm for tellurite glasses. Hence only the 290 nm fluorescence is strongly absorbed in the Sb-silicate glass, both the 290 nm and 360 nm are strongly absorbed in the tellurite (leaving the 480 nm) whilst none are strongly absorbed in the germanate. In addition, FIG. 3 shows that the Sb-silicate glass demonstrates UV absorption from below about 350 nm, whereas the germanate glass absorption edge is nearer 300 nm. The absorption of the UV light by the glass materials creates refractive index changes in the respective glass materials.

Glasses may undergo changes to their optical properties when exposed to UV light, one possible result being the creating of permanent defects within the glass structure. This process is often accompanied by a significant change in the glass transmission spectrum, particularly in the UV/visible region. Whether this process occurs is strongly dependent on the glass composition and the particular details of the glass processing. However in an optimized glass, it is possible to induce a significant refractive index change in the glass through the creation of these defects, a well-known phenomenon expressed through the Kramers-Kronig relationship. This index change may be used in the formation of waveguide structures and in writing gratings.

Figure 8:
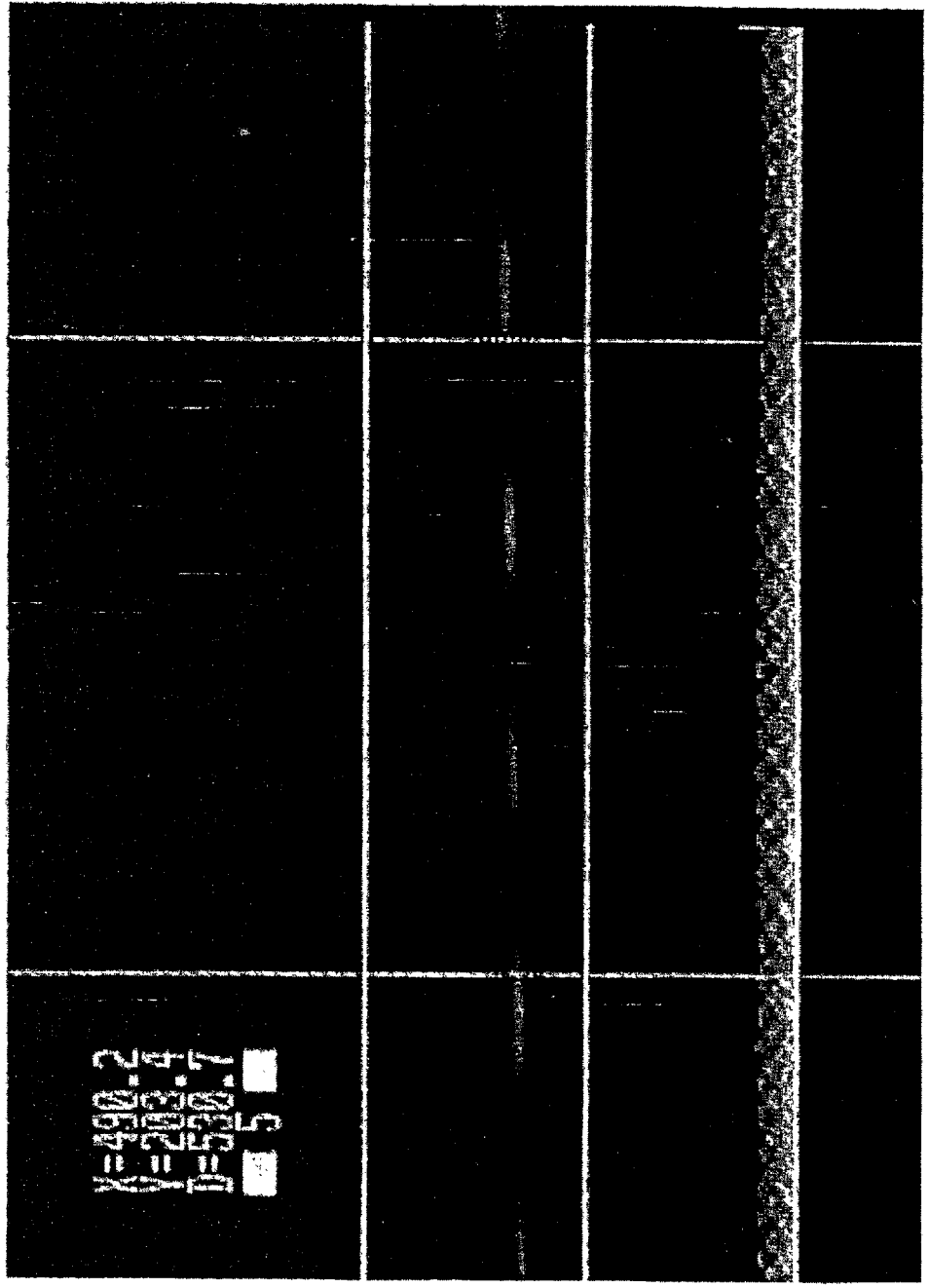
FIG. 8 is a graph showing the interference pattern along an Sb-silicate fiber for $Tm^{3+}$ doped Sb-silicate fiber.

FIG. 8 shows the blue up-conversion fluorescence from a thulium doped Sb-silicate fiber, where we clearly see a periodic structure to the up-conversion fluorescence. The periodic intensity variation in the up-conversion fluorescence arises from the interference of the pump modes propagating due to the multi-mode nature of the fiber.

Figure 5A:
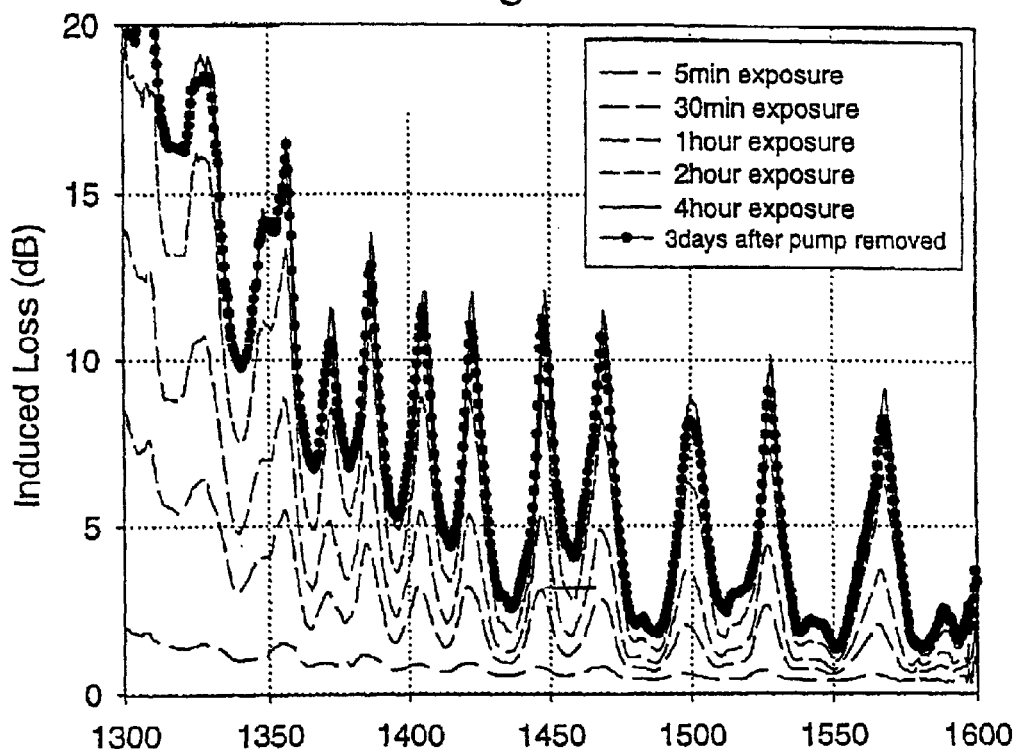
FIG. 5A is a graph showing the measured change in transmission as a function of signal wavelength for $Tm^{3+}$ doped Sb-silicate multi-moded fiber with a 4 μm core.
Figure 5B:
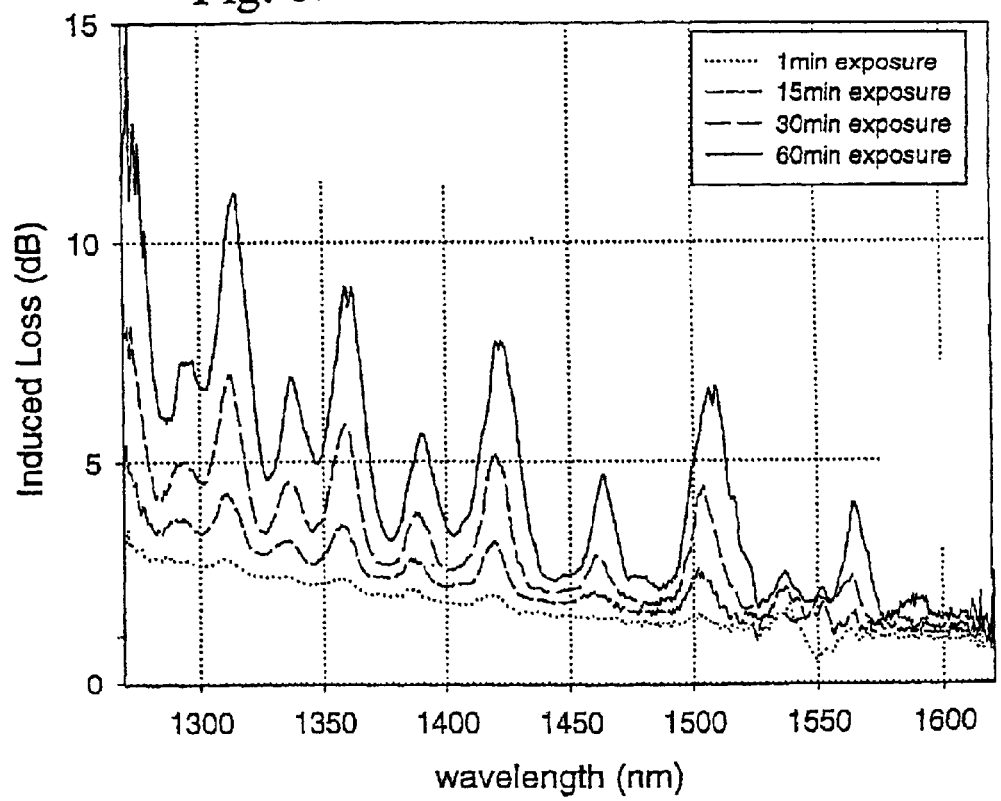
FIG. 5B is a graph showing the change in transmission as a function of signal wavelength for $Tm^{3+}$ doped Sb-silicate multi-moded fiber with a 3 μm core.
Figure 6:
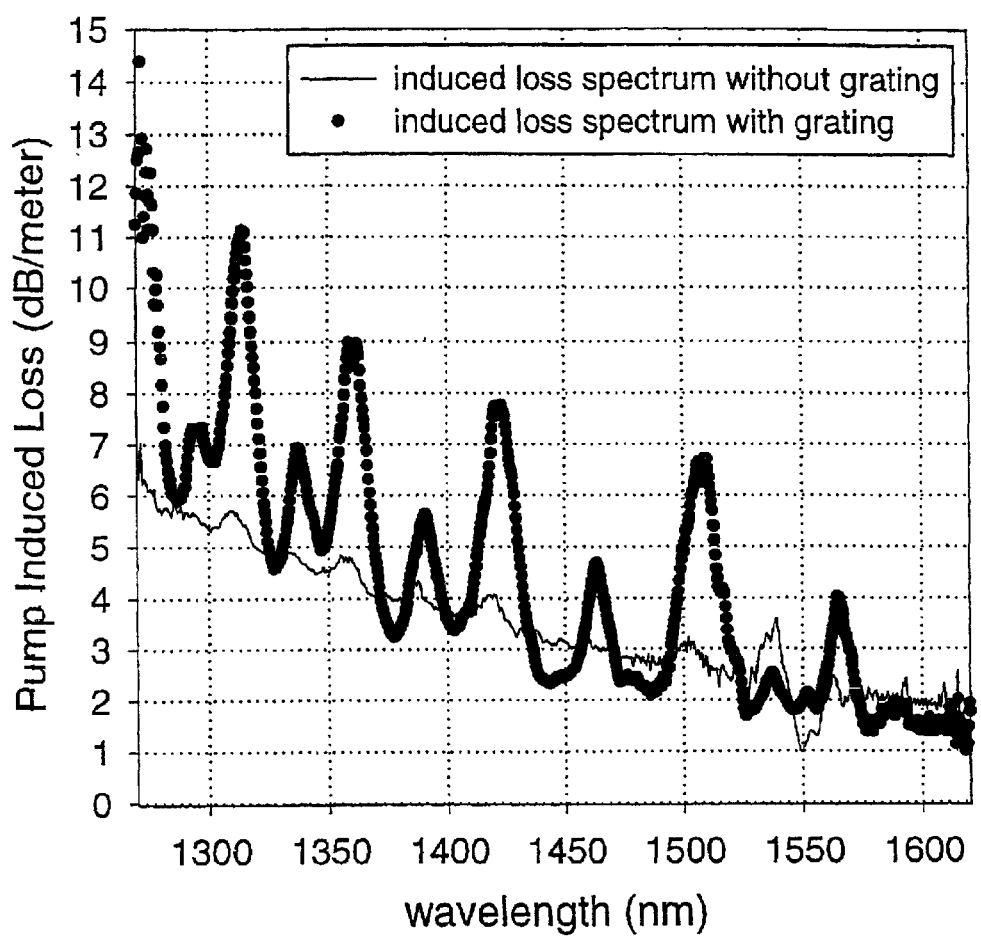
FIG. 6 is a graph showing the induced loss as a function of signal wavelength for $Tm^{3+}$ doped Sb-silicate fiber.

FIGS. 5A, 5B, and 6 show the affect of the refractive index changes caused by the present invention. Specifically, FIGS. 5A and 5B show the growth of a grating within the core of the optical fiber. The induced loss spectrum shows the growth of an exponential like tail decreasing in magnitude at longer wavelengths (the induced loss tail increases into the visible and UV). Superimposed on this is a series of sharp peaks (easily 10 dB peak to peak) almost periodic in wavelength. This structure arises from the periodic intensity variation seen in the up-conversion fluorescence shown in FIG. 8, which in turn has created a spatial modulation in the density of UV induced defects. The associated refractive index change also has a periodic structure determined by the pump radiation interference pattern, showing a formed grating with a period corresponding to the up-conversion fluorescence of FIG. 8. In particular, induced loss in dB/m, indicating the presence of a refractive index change, is shown for a Sb-silicate glass fiber 1 meter long with a grating structure written in a multi-mode 4 μm core (FIG. 5A), with a grating structure and a 3 μm core (FIG. 5B) and without a grating structure in FIG. 6.

Each of FIGS. 5A, 5B, and 6 show that induced loss and associated refractive index changes occur due to the present invention. The induced loss is due to semi-permanent defects in the substrate 20 caused by the glass absorbing UV radiation. A periodic modulation of the refractive index change is set up in these fibers by the intensity modulation of the pump radiation due to interference of the modes in the fiber (i.e. a single mode fiber would not have this periodic index modulation nor the grating structure shown in FIGS. 5A and 5B). This is more clearly shown in FIG. 6, where the loss spectrum for the defects (e.g. not a grating and a defect spectrum) is shown for comparison. The actual nature of the defects will depend strongly on the substrate material (e.g., the glass or polymer composition) as well as the details of the processing of the glass. By way of example but not by way of limitation, defects may include Ge E' centers in a germanate glass. As would be readily apparent to one skilled in the art, other defects are possible depending on the material.

The present invention also works to create local refractive index changes in organically modified photopolymerizable glasses, a class of composite materials where a photoinitiator and monomer are dispersed into the glass matrix during a melting process. Upon exposure to UV/visible light, the polymerization process proceeds and can result in large local refractive index changes given the correct composition of glass matrix and resulting polymer. This phenomenon is described in Pavel Cheben, *A Photopolymerizable Glass With Diffraction Efficiency Near 100% For Holographic Storage,* Applied Physics Letters, Vol. 78 No. 11 (2001), which is incorporated by reference herein in its entirety. The thulium ion up-conversion process can be used to create enough visible/UV light to stimulate the local polymerization process and hence result in a local index change. In regions where the IR pump light intensity is less than a predetermined value (e.g. outside the focal spot), the polymerization process would not proceed.

The present invention can create refractive index changes in less time than a conventional UV technique. Each of FIGS. 5A and 5B shows the induced loss measured immediately after various exposure times. Exposure of the optical fiber to IR radiation for only a couple of hours effectively created the refractive index change along the 1 meter optical fiber, dramatically reducing the manufacturing times when compared to conventional UV techniques requiring several hours of exposure per 10 cm section. FIG. 5A further shows that a refractive index change created by the present invention is semi-permanent, i.e., that the refractive index change was present three days after being formed according to the present invention.

FIG. 6 shows the refractive index change with and without a superimposed grating structure. FIG. 6 shows the induced loss measured on multi-mode (grating formatted) and single-mode (no grating), the loss spectrum directly attributable from the refractive index change in the optical fiber. This refractive index change will typically have a magnitude of about 0.001 to about 0.01.

Figure 7:
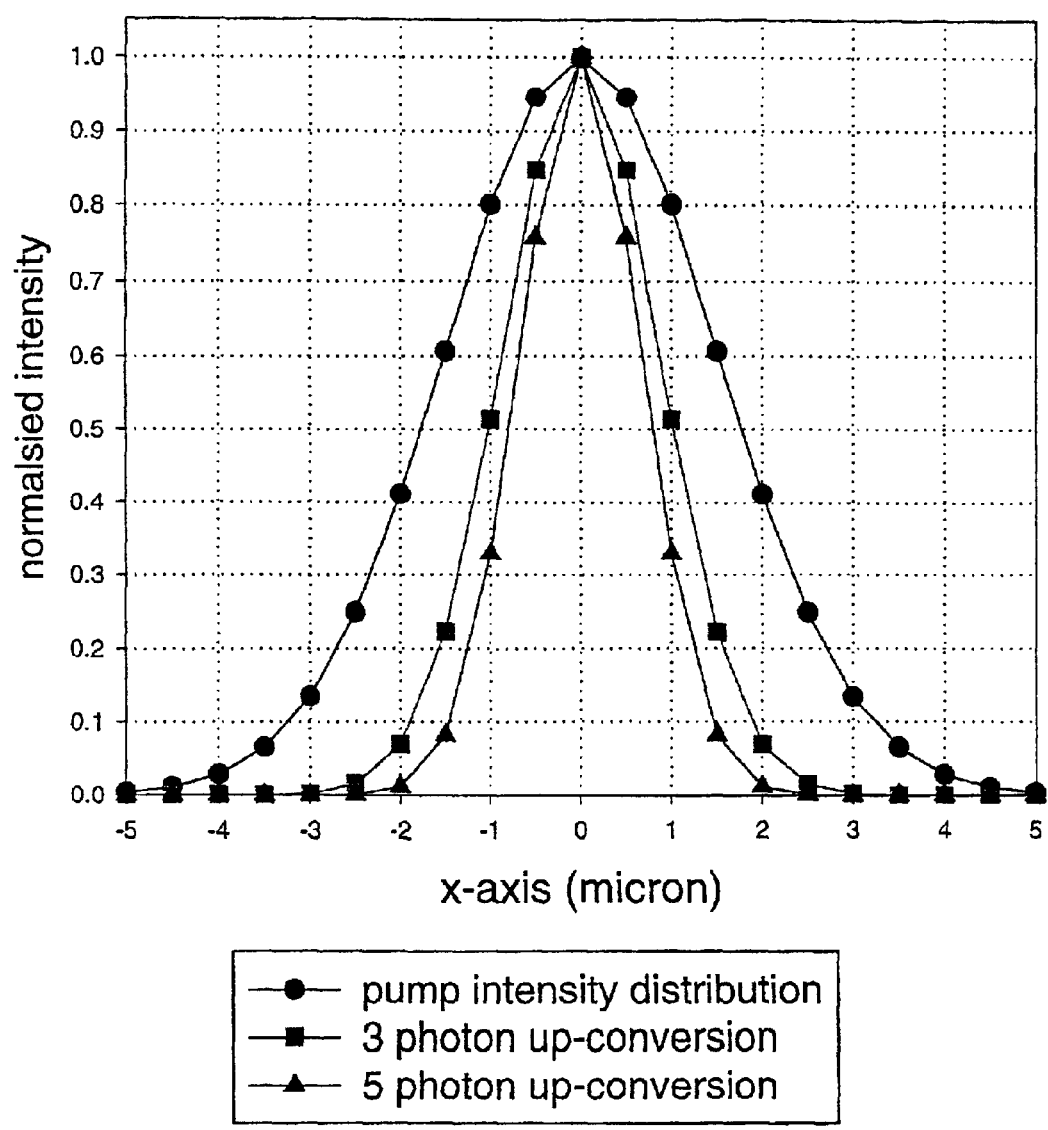
FIG. 7 is a graph showing the Gaussian beam intensity for an IR pump and the intensity profiles for three photon and five photon up-conversion

Another advantage of the present invention derives from the pump intensity (I) dependence of the up-conversion process. For example, a three step process will normally follow $I^3$ and a five step process $I^5$. An example of this is shown in FIG. 7, where the Gaussian beam intensity for the IR pump is shown, as well as the intensity profiles for three photon and five photon up-conversion. The smaller area defined by the up-conversion process will give rise to a more localized refractive index change, offering an advantage in high density optical memory applications.

The present invention allows for more precise control of the location and magnitude of changes in the refractive index. The inventor has found that up-conversion of IR radiation to create refractive index changes involves a refractive index change in a more concentrated region than two photon absorption of blue light despite the longer writing wavelength. This concentration (localization) is at least partially attributable to the absorption of the UV emission by the glass in close physical proximity to the excited ion dopants. Typically, two photon absorption of blue light does not utilize ion dopants, as dopants are not required to increase the absorption of the blue light. Therefore, the refractive index change caused by two photon absorption of blue light is concentrated in the region of exposure. The inventor has found that the present invention can benefit from concentrating the ion dopants in a region where a high degree of refractive index change is sought, which allows an unprecedented control over the location and rate of change of the refractive index changes created in the substrate 20. Concentrated refractive index writing allows for the creation of high-density optical storage devices utilizing the present invention.

The present invention allows for more precise control of the magnitude of changes in the refractive index changes by controlling the ambient temperature. Thus, the ambient temperature may be selected to further control the up-conversion process, and is selected based on the desired refractive index parameters. Generally, an increase in ambient temperature weakens the refractive index change, and a decrease in ambient temperature sharpens the refractive index changes. The refractive index changes are typically semi-permanent, but may be removed by an appropriate heat treatment, the actual temperature depending on the substrate but usually approaching the transition temperature. Heat treatment allows for optical fibers with improperly formed refractive index changes to be reworked rather than discarded, improving the efficiency of the manufacturing process.

In contrast to the conventional two photon absorption technique, the present invention can be used to create refractive index changes in glasses with red-shifted absorption edges. For example, as shown in FIG. 4, tellurite (a red-shifted glass) absorbs the UV light emitted by $Tm^{3+}$ ions. Thus, the present invention provides the ability to make refractive index changes in glasses that could not be changed using the conventional two photon absorption technique.

Unlike conventional UV techniques, the present invention can be used to create refractive index changes in optical fibers longer than 10 cm with a single exposure. By way of example, the present invention has been used to create refractive index changes in 4 µm optical fiber 1 meter long. Further, as IR sources are relatively inexpensive in comparison to high power blue lasers, the present invention can typically be implemented at a lower cost than two photon blue laser manufacturing techniques.

Thus, a method for creating refractive index changes in a substrate has been described according to the present invention. Many modifications and variations may be made to the techniques and structures described and illustrated herein without departing from the spirit and scope of the invention. Accordingly, it should be understood that the methods and apparatus described herein are illustrative only and are not limiting upon the scope of the invention.

What is claimed is:

1. A method for creating refractive index changes in a substrate comprising:
    irradiating the substrate with a pump radiation of wavelength greater than ultra-violet (UV) radiation,
    generating UV radiation within said substrate responsive to said radiation such that the change in the refractive index of the substrate is generated responsive to said UV radiation.

2. The method of claim 1, wherein the pump radiation is infrared (IR) radiation.

3. The method of claim 1, wherein the pump radiation is visible light.

4. The method of claim 2, wherein the substrate comprises a glass doped with rare earth ions.

5. The method of claim 4, wherein the rare earth ions comprise at least one of $Pr^{3+}$, $Er^{3+}$, $Eu^{3+}$, $Nd^{3+}$, $Ho^{3+}$, $Sm^{3+}$, $Tb^{3+}$, $Dy^{3+}$, and $Tm^{3+}$ ions.

6. The method of claim 4, wherein the rare earth ions comprise $Tm^{3+}$ ions and the IR radiation increases the $^1G_6$ level population of the rare earth ions.

7. The method of claim 6, wherein at least one of the $^1D_2$ level population and the $^3P_0$ level population of the rare earth ions is increased by up-conversion of the $^1G_4$ level population.

8. The method of claim 7, wherein the rare earth ion emits the UV radiation.

9. The method of claim 1, wherein UV radiation creates defects in the substrate which cause a change in the refractive index of the substrate.

10. The method of claim 7, further comprising the step of: setting temperature conditions at which up-conversion in a substrate component takes place.

11. The method of claim 2, wherein the step of irradiating the substrate is performed by at least one pump IR emitting device for generating IR radiation with at least one pre-selected wavelength which generates a population up-conversion in a substrate component.

12. The method of claim 3, wherein the step of irradiating the substrate is performed by at least one pump visible light emitting device for generating visible light radiation with at least one pre-selected wavelength which generates a population up-conversion in a substrate component.

13. The method of claim 11, wherein the IR radiation contains at least one wavelength in the range of 600 nm to 1500 nm.

14. The method of claim 13, wherein the IR radiation contains at least one wavelength in the range of 1000 nm to 1250 nm.

15. The method of claim 14, wherein the IR radiation contains at least a wavelength of 1060 nm.

16. The method of claim 14, wherein the IR radiation contains at least a wavelength of 1120 nm.

17. The method of claim 1, wherein the substrate comprises a rare earth ion doped optical fiber.

18. The method of claim 1, wherein the substrate comprises a Sb-silicate glass.

19. The method of claim 1, wherein the substrate comprises a germanate glass.

20. The method of claim 1, wherein the substrate comprises a tellurite glass.

21. A waveguide formed by the process of claim 1.

22. A substrate comprising:
    a substrate matrix material;
    at least one type of rare earth ion dopant in the matrix material; and
    at least one defect in the matrix material which affects a refractive index of the substrate,
    wherein said at least one defect was created by ultra-violet (UV) radiation emission from the rare earth ion dopants responsive to pump radiation at a wavelength longer than said UV radiation.

23. The substrate of claim 22, wherein the UV radiation is created by an up-conversion process which converts said pump radiation to UV radiation.

24. The substrate of claim 22, wherein the rare earth ion dopants comprises $Tm^{3+}$ ions.

25. The substrate of claim 24, wherein the substrate comprises an optical fiber, whose core is doped with the $Tm^{3+}$ ions.

26. The substrate of claim 24, wherein the substrate comprises a Sb-silicate glass.

27. The substrate of claim 24, wherein the substrate comprises a germanate glass.

28. The substrate of claim 24, wherein the substrate comprises a tellurite glass.

29. A method of making a glass substrate comprising the steps of:
    doping the glass substrate with fluorescent ions; and
    pumping radiation into the glass substrate, wherein ultra-violet (UV) radiation is generated in said substrate by said fluorescent ions responsive to said pump radiation to create defects in the substrate such that a change in a refractive index is generated.

30. The method of claim 29 wherein the pump radiation is infrared (IR) radiation.

31. The method of claim 29 wherein the pump radiation is visible light radiation.

32. The method of claim 29, wherein the glass substrate comprises an optical fiber doped with $Tm^{3+}$ fluorescent ions.

33. The method of claim 30, where the step of pumping IR radiation is performed by a semiconductor diode.

34. The method of claim 30, wherein the step of pumping IR radiation is performed by a Raman pump laser.

* * * * *